United States Patent [19]

Pebler

[11] 4,394,240
[45] Jul. 19, 1983

[54] COMBINED SULFUR OXIDE/OXYGEN MEASURING APPARATUS

[75] Inventor: Alfred R. Pebler, Penn Hills, Pa.

[73] Assignee: Westinghouse Electric Corp., Pittsburgh, Pa.

[21] Appl. No.: 358,769

[22] Filed: Mar. 16, 1982

[51] Int. Cl.³ .......................................... G01N 27/58
[52] U.S. Cl. ....................................204/412; 204/1 T
[58] Field of Search ........................... 204/195 S, 1 S; 427/125

[56] References Cited

U.S. PATENT DOCUMENTS 3,652,427  3/1972  Flood et al. ..................... 204/195 S
4,128,458  12/1978  Obiaya .............................. 204/195 S
4,282,078  8/1981  Chamberland et al. ......... 204/195 S Primary Examiner—Howard S. Williams
Assistant Examiner—Terryence Chapman
Attorney, Agent, or Firm—M. P. Lynch

[57] ABSTRACT

Oxygen ion and oxy-anion conductive solid electrolyte, electrochemical cells are combined to form a single gas measuring apparatus having a common internal gas reference and developing electrical signals from which the partial pressure of oxygen and an anhydride of a monitored gas environment can be determined.

4 Claims, 2 Drawing Figures

COMBINED SULFUR OXIDE/OXYGEN MEASURING APPARATUS

BACKGROUND OF THE INVENTION

Solid state detectors have been developed for measuring anhydrides, i.e., $SO_X$, $NO_X$, etc., present in monitored gas environments such as the stack, or flue, gas environments of a combustion process. The solid state detectors include a solid electrolyte element containing oxy-anions of the particular anhydride to be detected. In most practical industrial applications, the detector requires compensation for changes in the oxygen content of the monitored gas environment and indeed it is often necessary to separately measure the oxygen content of the monitored gas environment. A suitable solid state sensor for anhydrides is described in U.S. Pat. No. 4,282,078, which has been assigned to the assignee of the present invention, and is incorporated herein by reference. The use of oxygen ion conductive solid electrolyte sensors for oxygen measurements is well known and is described in detail in the U.S. Pat. No. Re. 28,792, which is assigned to the assignee of the present invention and incorporated herein by reference.

SUMMARY OF THE INVENTION

There is described herein with reference to the accompanying drawings a multi-sensor, high-temperature gas measuring apparatus for simultaneously monitoring the anhydride and oxygen concentration in a monitored gas environment such as the flue gas of a utility or an industrial boiler. The multi-sensor apparatus consists of a solid electrolyte enclosure having a cavity therein and a solid reference material positioned within the cavity and responding to elevated temperatures by thermally decomposing to produce a reference gas suitable for the anhydride to be measured. The walls of the solid electrolyte enclosure are comprised of solid electrolyte material such that the positioning of a reference electrode on the inner surface of said enclosure and three sensing electrodes on the opposite surfaces of the solid electrolyte enclosure members creates three solid electrolyte electrochemical cells. A first cell generates an electrical signal indicative of the combination of the anhydride and the oxygen content of a monitored gas environment brought into contact with the enclosure; the second cell develops a measurement of the oxygen content of the monitored gas; and the third cell, which is isolated from the monitored gas environment and exposed to an oxygen reference environment such as air, provides an indication of the variation in the oxygen content of the reference gas within the enclosure. Electrical signals are then supplied to suitable circuitry, such as a microprocessor, to develop signals indicative of the absolute partial pressure of both the anhydride and the oxygen within the monitored gas environment.

DESCRIPTION OF THE DRAWINGS

The invention will become more readily apparent from the following exemplary description in connection with the accompanying drawings.

DESCRIPTION OF THE PREFERRED EMBODIMENT

As described above with reference to the above cited patents, the selection of ther material composition for a solid electrolyte element of an anhydride detector is determined on the basis of the particular anhydride to be monitored. Similarly, in the implementation of the disclosed invention, the selection of the solid reference composition is likewise determined by the anhydride to be monitored. For the purposes of discussion, it will be assumed in the description of the following typical implementation of the invention that the anhydride to be monitored is $SO_3$ in an equilibrated $SO_2$—$SO_3$—$O_2$ containing gas mixture. The equilibrium partial pressure of $SO_3$, $p_{SO_3}$, is thus related to the total $SO_X$ pressure $$p_{SOX} = p_{SO_2} + p_{SO_3} \tag{1}$$

by the relationship $$p_{SOX} = p_{SO_3}(1 + K p_{O_2}^{-\frac{1}{2}}), \tag{2}$$

where K is the known equilibrium constant of the reaction $$SO_3 = SO_2 + \tfrac{1}{2}O_2 \tag{3}$$

It is recognized that the following teachings are equally and readily applicable to solid state sensor compositions suitable for monitoring other anhydrides.

Figure 1:
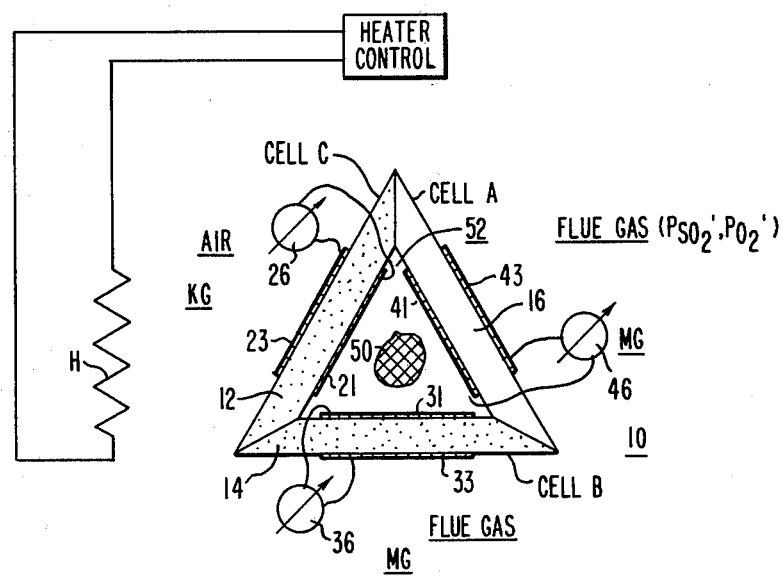
FIG. 1 is a conceptual illustration of the invention.

The inventive concept as depicted in FIG. 1 comprises a solid electrolyte enclosure 10 consisting of oxygen ion conductive solid electrolyte wall members 12 and 14 and a third solid electrolyte wall element 16 comprised of a composition containing oxy-anions of the gaseous anhydride to be analyzed, i.e., $SO_3$. The composition of the wall element 16 is made up of an alkali metal salt, which, for the purpose of the illustration may typically be $K_2SO_4$ as is described in detail in the above reference U.S. Pat. No. 4,282,078. The oxygen ion conductive solid electrolyte composition of the wall elements 12 and 14 may typically consist of stabilized zirconia as is described in detail in the above referenced U.S. Pat. No. Re. 28,792. The combination of the reference electrode 21 and sensing electrode 23 on opposite surfaces of the solid electrolyte wall element 12 form an oxygen ion measuring electrochemical cell C. The combination of the reference electrode 31 and sensing electrode 33 on opposite surfaces of the oxygen ion conductive solid electrolyte wall element 14 form an oxygen ion conductive solid electrolyte electrochemical cell B. The combination of the reference electrode 41 and sensing electrode 43 on opposite surfaces of the oxy-anion solid electrolyte wall 16 from an oxy-anion solid electrolyte electrochemical cell A. The measuring concept illustrated in FIG. 1 utilizes the temperature dependent decomposition of a suitable sulfate element 50 to create an $SO_3$ reference gas environment within the cavity 52 by the reversible decomposition reaction $$MSO_4 = MO + SO_3, \tag{4}$$

where M may be Mg, Mn or $Ag_2$. The resulting $SO_3$ reference pressure is given by $$p_{SO_3}'' = K_{SO_3}, \tag{5}$$

where $K_{SO_3}$ is the known temperature-dependent equilibrium constant of reaction (4). The SO$_3$ constituent within the cavity 52 combines with the oxygen constituent within the cavity 52 to provide both the oxygen reference for the operation of the electrochemical cells B and C, and the SO$_3$ reference for the operation of electrochemical cell A.

The operating temperature of the combined electrochemical cell sensor of FIG. 1 is typically in the range of about 600° C. and 800° C. The heating of the sensor is provided by a suitable heating source H.

The sensing electrodes 33 and 43 of the electrochemical cells B and A are exposed to the monitored gas environment MG containing unknown partial pressures of O$_2$ and SO$_3$. The sensing electrode 23 of the electrochemical cell C is exposed to a gas environment KG of known oxygen partial pressure such as air which has an oxygen partial pressure $p_{O_2}=0.21$ atmospheres. The electrical signal generated by the oxygen ion conductive solid electrolyte electrochemical cell C is given by the following well known Nernst equation:

$$E_C = \frac{RT}{4F} \ln \frac{0.21 \text{ (for air)}}{p_{O_2}''} \quad (6)$$

where $p_{O_2}''$ is the unknown partial pressure of oxygen in the cavity 52.

The electrical signal generated by the oxygen ion conductive solid electrolyte cell B corresponds to the following Nernst equation:

$$E_B = \frac{RT}{4F} \ln \frac{p_{O_2}'}{p_{O_2}''} \quad (7)$$

where $p_{O_2}'$ is the unknown partial pressure of oxygen in the monitored environment MG and $p_{O_2}''$ is the unknown partial pressure of oxygen in the cavity 52.

The EMF signal developed by the oxy-anion conductive solid electrolyte electrochemical cell A corresponds to the following Nernst equation:

$$E_A = \frac{RT}{2F} \ln \frac{p_{SO_3}' p_{O_2}'^{\frac{1}{2}}}{K_{SO_3} p_{O_2}''^{\frac{1}{2}}} \quad (8)$$

The above EMF measurements are schematically illustrated in FIG. 1 as being realized through the use of EMF measuring circuits 26, 36 and 46 connected across the electrodes of electrochemical cells C, B and A, respectively. A suitable electrode material for the electrochemical cells is platinum.

According to equation (8), the EMF signal developed by the electrochemical cell A depends both on the partial pressures of the sulfur oxide ($p_{SO_3}'$) and oxygen ($p_{O_2}'$). The EMF signal developed by the electrochemical cell B under the same operating conditions as electrochemical cell 44 provides an independent measurement of the oxygen partial pressure ($p_{O_2}'$) of the monitored gas environment MG and thus by suitable combination of the EMF signals developed by the electrochemical cells A and B, a measurement of the unknown partial pressure of SO$_3$ in the monitored gas environment MG can be obtained as follows:

$$E_{SO_3} = E_A - E_B = \frac{RT}{2F} \ln \frac{p_{SO_3}'}{K_{SO_3}} \quad (9)$$

In conventional gas measuring probes it is necessary to isolate the reference gas environment from the monitored gas environment to avoid unpredictable drift in the measurement signal. This problem of sealing is overcome in the concept of FIGS. 1 and 2 through the use of the electrochemical cell C since the oxygen of the reference gas cavity 52 is referenced to ambient air at all times. Thus, the construction of the enclosure 10 need only minimize diffusional loss of SO$_3$ from the reference gas cavity 52. The combination of equations (2) and (3) yields the unknown partial pressure of oxygen in the monitored gas environment MG in accordance with the following equation:

$$E_{O_2} = E_B - E_C = \frac{RT}{4F} \ln \frac{p_{O_2}'}{0.21} \quad (10)$$

The total SO$_X$ partial pressure is then obtained from the determinations of $p_{SO_3}'$ and $p_{O_2}'$ with equation (2).

The implementation of circuitry to effect the above computations can be readily achieved through existing circuit designs, including the use of a microprocessor.

Figure 2:
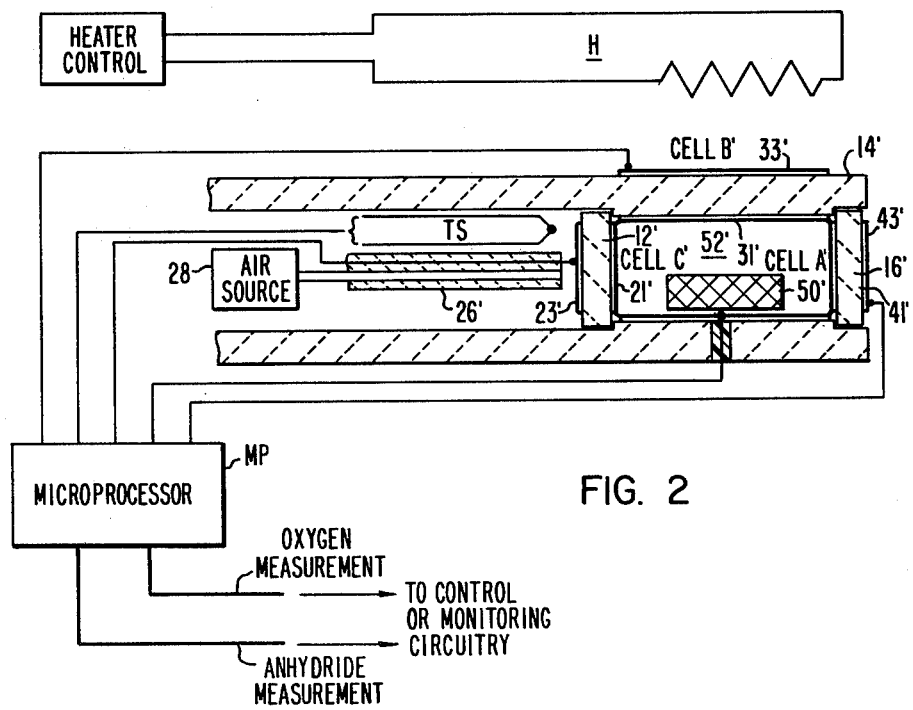
FIG. 2 is a sectioned schematic illustration of a gas measuring probe incorporating the inventive concept illustrated in FIG. 1.

A practical multi-sensor gas probe based on the concept of FIG. 1 is illustrated in the sectioned, schematic embodiment of FIG. 2. A tubular member of oxygen ion conductive solid electrolyte material, i.e., stabilized zirconia, 14' in combination with reference electrode 31' and sensing electrode 33' form the oxygen ion conductive electrochemical cell B' which is responsive to the oxygen partial pressure of the monitored gas environment MG and develops an EMF signal $E_B'$ which is supplied to a microprocessor circuit MP. The reference gas cavity 52', which contains the solid reference element 50', is formed by positioning an oxygen ion conductive solid electrolyte element 12' and an oxy-anion conductive solid electrolyte element 16' in spaced apart relationship within the tubular member 14'. As described above with reference to FIG. 1, the oxy-anion solid electrolyte member 16' is, for the purpose of discussion, a material that is responsive to the SO$_3$ partial pressure of the monitored gas environment MG, and is typically implemented through the use of a K$_2$SO$_4$ composition. The reference electrode 41' and the sensing electrode 43' disposed on opposite surfaces of the electrolyte element 16' form the oxy-anion solid electrolyte electrochemical cell A'. An oxygen reference solid electrolyte electrochemical cell C' is formed by the combination of the oxygen ion conductive, i.e., stabilized zirconia, solid electrolyte element 12' in combination with the reference electrode 21' and the sensing electrode 23'. A gas environment, i.e. air, of known and stable oxygen content KG is maintained in contact with the sensing electrode 23' of the electrochemical cell C' by supplying a flow of air through an inlet tube 26' from an air reference source 28'. While the reference electrodes of the electrochemical cells A', B' and C' are identified as separate reference electrodes, a single reference electrode coating of a suitable material, i.e., platinum, may be applied to the inner surfaces of the reference gas cavity 52' defined by the electrolyte elements 12', 14' and 16'. A single electrical lead would then connect the common reference electrode to the microprocessor circuit MP.

In order to account for the operating cell temperature, as reflected in the Nernst equations, a temperature sensor TS provides an electrical signal to the microprocessor circuit MP. The microprocessor circuit MP performs the calculations identified in the above equations and provides output signals indicative of the absolute partal pressures of both $O_2$ and $SO_X$ of the monitored gas environment MG. Thse signals are available for indication and control purposes. A suitable microprocessor for use in this application is the KIM-1 microprocessor which is commercially available from MOS technology, Inc.

I claim:

1. A multi-sensor gas measuring apparatus for generating signals indicative of the partial pressure of oxygen and the partial pressure of a selected anhydride, i.e., $SO_X$, $NO_X$, etc. of a monitored gas environment comprising, first and second solid electrolyte electrochemical cells each cell including an oxygen ion conductive solid electrolyte element having a sensing electrode and a reference electrode disposed on opposite surfaces thereof, a third solid electrolyte electrochemical cell including a solid electrolyte element containing oxyanions of the selected anhydride having a sensing electrode and a reference electrode disposed on opposite surfaces thereof, said first, second and third solid electrolyte electrochemical cells being combined to form an enclosure having a cavity therein, a reference composition of said selected anhydride and oxygen being located within said cavity, said reference electrodes of said first, second and third solid electrolyte electrochemical cells being exposed to said reference composition, said sensing electrode of said first solid electrolyte electrochemical cell being exposed to a gas environment of known oxygen partial pressure, said first cell generating a signal indicative of the oxygen partial pressure of the reference composition, said sensing electrodes of said second and third cells being exposed to said monitored gas environment, said second cell generating a signal indicative of the difference in oxygen partial pressure between the monitored gas environment and the reference composition, said third cell generating a signal indicative of the difference between the partial pressure of the combination of oxygen and the selected anhydride in the monitored gas environment and the partial pressure of the combination of oxygen and the selected anhydride in the reference composition, and circuit means connected to said first, second and third cells and responding to the signals generated by providing an indication of both the partial pressure of oxygen and the partial pressure of the selected anhydride within said monitored gas environment.

2. A multi-sensor gas measuring apparatus as claimed in claim 1 wherein said reference composition includes a salt containing the selected anhydride and oxygen, and heating means for heating said salt element to produce temperature dependent decomposition of said salt element to produce a reference gas containing the selected anhydride.

3. A multi-sensor gas measuring apparatus as claimed in claim 2 wherein the oxygen of the reference composition within said cavity is referenced at all times to the known oxygen partial pressure gas environment contacting the sensing electrode of said first cell, the combination of said first, second and third cells to form said enclosure being such as to minimize diffusional loss of the selected anhydride reference gas from said cavity.

4. A multi-sensor gas measuring apparatus as claimed in claim 1 wherein said second cell comprises an open ended tubular solid electrolyte element with said sensing electrode disposed on the outer surface and said reference electrode disposed on the inner surface, said third cell comprising a disc-shaped solid electrolyte element secured within the open end of said tubular solid electrolyte element of said second cell, said sensing electrode of said third cell being disposed on a surface of said disc-shaped electrolyte element outside said tubular solid electrolyte element, and said reference electrode of said third cell being disposed on a surface of said disc-shaped electrolyte element inside said tubular solid electrolyte element, said first cell comprising a disc-shaped electrolyte element positioned within said tubular solid electrolyte element of said second cell and spaced apart from the disc-shaped solid electrolyte element of said third cell to form said cavity, the reference electrodes of said first, second and third cells being exposed to the reference composition within said cavity, the sensing electrode of said first cell being exposed to a gas environment of known oxygen partial pressure maintained within said tubular solid electrolyte element but remote from said cavity.

* * * * *